United States Patent [19]

Rosenberger et al.

[11] 4,044,028

[45] Aug. 23, 1977

[54] PREPARATION OF α,β-UNSATURATED ALDEHYDES OR KETONES

[75] Inventors: Michael Rosenberger, Caldwell; Gabriel Saucy, Essex Fells, both of N.J.

[73] Assignee: Hoffmann-La Roche Inc., Nutley, N.J.

[21] Appl. No.: 723,375

[22] Filed: Sept. 15, 1976

Related U.S. Application Data

[62] Division of Ser. No. 468,836, May 10, 1974, Pat. No. 4,000,131.

[51] Int. Cl.$^2$ ............................................. C07D 303/06
[52] U.S. Cl. ................................................. 260/348.11
[58] Field of Search ..................................... 260/348 R Primary Examiner—Norma S. Milestone
Attorney, Agent, or Firm—Samuel L. Welt; Bernard S. Leon; William H. Epstein

[57] ABSTRACT

Homologation of α,β-polyene unsaturated aldehydes and ketones to form α,β-unsaturated aldehydes via epoxidation of the ketone or aldehyde and intermediates in this process such as β,γ-unsaturated polyene aldehydes.

1 Claim, No Drawings

4,044,028

PREPARATION OF α,β-UNSATURATED ALDEHYDES OR KETONES

BACKGROUND OF THE INVENTION

This is a division of application Ser. No. 468,836 filed May 10, 1974, and now U.S. Pat. No. 4,000,131, issued Dec. 28, 1976.

In the past, ketones has been converted to epoxides with sulfonic ylides. See Corey, et al. (J. Am. Chem. Soc, 87, 1353; and House, Modern Synthetic Reactions, Second Ed. W. A. Benjamin, Inc., Menlo Park, Calif., pg. 717, 1972. While this process has been utilized to epoxidize ketones, it has not been applied to polyene unsaturated ketones containing an unsaturation at the α,β position. Nor has this been applied to a process for producing α,β-unsaturated polyene aldehydes by homologation of aldehydes or ketones.

The α,β-unsaturated polyene aldehydes are very important compounds owing to their use as intermediates in the preparation of vitamins, carotenoids, and odor imparting compounds. However, the synthesis of these materials has met with some difficulty due to low yields and contaminating side products. As reported by Thomas, on page 52 of *Terpenoids and Steroids,* Specialist Periodical Reports, Vol. 3, published by Chemical Society, Burlington House, London, England, a good synthesis for α,β-unsaturated aldehydes such as β-cyclocitral "is indeed desired".

In the past, the major method for synthesizing α,β-unsaturated polyene aldehydes has been from lower polyene, α,β-unsaturate aldehydes or ketones by the Darzens reaction. See Isler, *Carotenoids,* Birkhauser Verlag, Basel and Stuttgart pp. 344-545. However, this process has suffered from the disadvantage that the yields are relatively poor especially after being carried out in large scale production. Therefore, a more efficient method for producing an α,β-unsaturated polyene aldehyde from lower α,β-unsaturated polyene aldehydes has long been desired in the art.

SUMMARY OF THE INVENTION

In accordance with this invention, it has been discovered that α,β-unsaturated aldehydes of the formula:

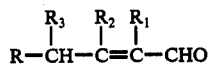
                       I-A wherein $R_1$, $R_2$ and $R_3$ are hydrogen or lower alkyl; R is an aliphatic hydrocarbyl containing at least one unsaturated double bond; cycloalkenyl, cycloalkenylsubstituted aliphatic hydrocarbyl wherein the hydrocarbyl contains at least one double bond and

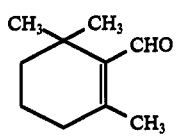
                       I-B are produced via epoxidation of a ketone or aldehyde of the formula:

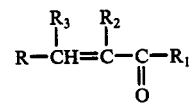
                       II-A wherein R, $R_1$, $R_2$ and $R_3$ are as above or

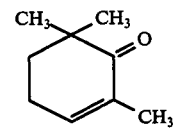
                     II-B

The compounds of formula I-A and I-B are a well-known class of α,β-unsaturated aldehydes and ketones useful in perfumary as odor imparting agents and in organic synthesis as intermediates in the preparation of perfumes, carotenoids and lipo-soluble vitamins. The process of this invention provides an efficient synthesis for producing the compounds of formulae I-A and I-B in high yields and high purity by homologation of lower α,β-unsaturated polyene aldehydes or ketones, avoiding the disadvantages of the Darzens synthesis.

Furthermore, this process provides an efficient method for producing β,γ-unsaturated polyene aldehydes, intermediates for the preparation of the compounds of formulae I-A and I-B in high yields and with a high degree of purity heretofore unobtained by conventional methods.

DETAILED DESCRIPTION

The term "halogen" as used throughout this specification, includes all four of the halogens, i.e. bromine, chlorine, fluorine and iodine with bromine and chlorine being especially preferred.

The term "alkali metal" as used in this specification includes any one of the alkali metals such as lithium, sodium, potassium, rubidum and caesium. The preferred alkali metals are sodium and potassium.

The term "alkaline earth metals" includes any of the conventional alkali earth metals such as calcium.

The term "lower alkyl" as used throughout this application comprehends branched and straight chain saturated aliphatic, hydrocarbyl groups containing from one to seven carbon atoms such as methyl, ethyl, propyl, isopropyl, etc. The term "hydrocarbyl" denotes a monovalent, straight chain aliphatic substituent consisting soley of carbon and hydrogen. The term "aliphatic hydrocarbyl group containing at least one unsaturated double bond" denotes aliphatic hydrocarbyl groups which are unsaturated in at least one position. Generally preferred are those unsaturated aliphatic hydrocarbyl groups which contain from two to 12 carbon atoms and have from one to four unsaturated double bonds such as:

vinyl;
allyl;
3,4-dimethyl-pent-3-en-1-yl;
1-ethyl-4-methyl-pent-4-en-1-yl;
4,8-dimethyl-nona-3,7-dien-1-yl;
4-methyl-penta-3-en-1-yl;
6-methyl-hept-5-en-1-yl; and
6-methyl-hept-1,5-dien-1-yl.

The term "cycloalkenyl" designates a cycloaliphatic substituent containing at least one double bond within the ring structure and which may be unsubstituted or substituted in one or more positions with a lower alkyl substituent. Generally preferred are the cycloalkenyl substituents which contain a 5 or 6 membered ring. Among the preferred cycloalkenyl substituents is:

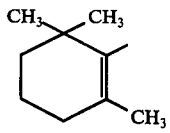

i.e. 2,6,6-trimethyl-cyclohex-1-en-1-yl'.

The term "cycloalkenyl substituted aliphatic hydrocarbyl wherein the hydrocarbyl contains at least one double bond" designates substituents where "cycloalkenyl" and "hydrocarbyl" are defined as above. Generally preferred are those cycloalkenyl substituted aliphatic hydrocarbyl wherein the hydrocarbyl contains at least one olefinic double bond and which have from seven to 20 carbon atoms. Among the preferred substituents are:

2 (2,6,6-trimethyl-cyclohex-1-en-1-yl)-vinyl;
6 (2,6,6-trimethyl-cyclohex-1-en-1-yl)-4-methyl-hex-1,3,5-trienyl; and
5(2,6,6-trimethyl-cyclohex-1-en-1-yl)-2-methyl-penta-1,3-dienyl.

Among the preferred compounds of formula I-A is a compound of the formula:

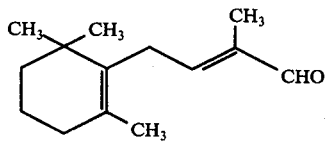

I-Ai

The compound of formula I-A is formed from the compound of formula II-A via the following intermediates:

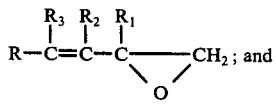

III-A

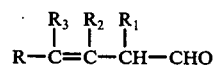

IV-A wherein R, $R_1$, $R_2$, $R_3$ are as above.

The compound of formula I-B is prepared from the compound of formula I via the following intermediates:

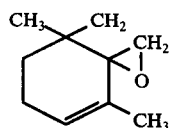

; and III-B

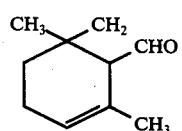

IV-B

Among the preferred compounds of formula III-A is a compound having the formula:

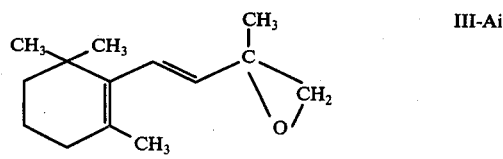

III-Ai

In accordance with a preferred embodiment of the process of this invention, the preferred α,β-unsaturated ketone which is 2,6,6-trimethylcyclohex-2-en-1-one is converted to the α,β-unsaturated epoxide 4,8,8-trimethyl-1-oxaspiro[2,5]oct-4-ene. This epoxide is then converted to the α,β-unsaturated aldehyde β-cyclocitral which is useful in synthesizing vitamin A. See pg. 333 of Isler, Carotenoids, Birkhauser Verlag, Switzerland, pps. 330–345.

Also in accordance with another preferred embodiment of the process of this invention, the α,β-unsaturated ketone, β-ionone is converted to the α,β-unsaturated epoxide, 1-(2,6,6-trimethyl-1-cyclohexenyl)-3-methyl-3,4-epoxy-but-1-ene. This epoxide is then converted to the α,β-unsaturated aldehyde, 1-(2,6,6-trimethyl-1-cyclohexyl)-3-methyl-2-buten-4-al, which is useful in synthesizing vitamin A. See Isler, supra, at pps. 344–345.

The compounds of formula II-A and II-B are converted to the compound of formula III-A and III-B respectively by treating either the compound of formula II-A or II-B with a sulfonium methylide of the formula:

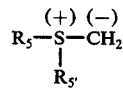

V wherein $R_5$ and $R_5'$ are independently aryl, methyl or taken together with their attached sulfur atom to form a 5 to 8 membered heterocyclic ring containing at least one additional oxygen hetero atom.

In the compound of formula V, $R_5$ can be any conventional aryl group. The term "aryl" denotes mononuclear aromatic hydrocarbon groups which can be unsubstituted or substituted in one or more positions with a lower alkyl group. Among the preferred aryl substituents are phenol, tolyl, etc.; with phenyl being especially preferred. Among the preferred compounds of formula V are dimethyl sulfonium methylide and diphenyl sulfonium methylide. Where $R_5$ and $R_5'$ form a heterocyclic ring, the preferred rings contain from 5 to 6 members which members consist only of carbon atoms in addition to the attached sulfur atom. On the other hand, the heterocyclic ring structure can contain an additional oxygen atom. Among the preferred heterocyclic ring structures are included tetrahydrothiophenyl and 1,4-oxo-thien-1-yl.

The reaction is carried out by reacting the compound of either the formula II-A or II-B with the sulfonium methylide in a conventional inert organic solvent. In generating the sulfonium methylide of formula V, any conventional means can be utilized such as disclosed by Corey, et al, in J. Chem. Soc., 87, 1353 (1965). In accordance with a preferred embodiment of this invention, the sulfonium methylide of formula V is prepared by first forming a suspension of a sulfonium salt of the formula:

wherein Y is a halide and $R_5$ and $R_5'$ are as above in dimethyl sulfoxide and tetrahydrofuran, then adding an alkali metal or alkaline earth metal dimethylsulfoxide salt at a temperature of from $-10°$ C. to $+10°$ C. to the suspension to form the compound of formula V. The compound of formula II-A or II-B can be then added to this suspension containing the compound of formula V to form the compound of formula III-A or III-B.

In carrying out this reaction step to produce the compound III-A or III-B, any conventional inert organic solvent can be utilized, such as tetrahydrofuran, dioxane, diethyl ether or dimethylsulfoxide. Preferably, this reaction is carried out in a mixture of dimethylsulfoxide and tetrahydrofuran. In carrying out this process, temperature and pressure are not critical, and any temperature from the freezing point of the reaction mixture to about 10° C. and atmospheric pressure can be suitably utilized. Preferably, this reaction is carried out at from $-80°$ C. to $+10°$ C. Preferably, this process is also carried out under an inert gas atmosphere, such as an argon or nitrogen.

The $\alpha,\beta$-unsaturated epoxide of formula III-A or III-B is converted to the $\alpha,\beta$-unsaturated aldehydes of formula I-A or I-B by treating the epoxide with a Lewis acid, and then isomerizing the resulting $\beta,\delta$-unsaturated aldehyde of formula IV-A and IV-B. Among the preferred compounds of formula IV-A is a compound having the formula:

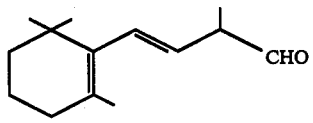

The epoxide of formula III-A or III-B is converted to the $\beta,\delta$-unsaturated aldehyde of formula IV-A or IV-B by treating the epoxides with a Lewis acid. Any conventional Lewis acid can be utilized in carrying out this reaction. Among the preferred Lewis acids are halides of metals such as magnesium, zinc, iron and aluminum. The particularly preferred Lewis acid in the reaction is magnesium bromide. This reaction is carried out in an inert organic solvent preferably ether. In this reaction, any conventional inert organic solvent can be utilized, such as the di(lower-alkyl) ethers, the aliphatic hydrocarbons, ethyl acetate or carbon tetrachloride. In this reaction, temperature and pressure are not critical, and any temperature of from about $-90°$ C. and $+50°$ C. and atmospheric pressure can be suitably utilized. Preferably, this reaction is carried out at room temperature, i.e. 15° to 30° C.

The $\beta,\delta$-unsaturated aldehyde of formula IV-A or IV-B can be isomerized to form the $\alpha,\beta$-unsaturated aldehyde of formula I-A or I-B by treating the aldehyde of formula IV-A or IV-B with an aqueous base. In this reaction, any conventional base can be utilized, such as the alkali metal and alkaline earth metal hydroxides, preferably the alkali metal hydroxides. This reaction can be suitably carried out in an inert, water-miscible, organic solvent, such as a lower alkanol or a di(lower) ether. Preferably, this reaction is carried out in the reaction medium in which the $\beta,\delta$-unsaturated aldehyde of formula IV-A or IV-B is formed. In this reaction, temperature and pressure are not critical, and the reaction can be suitably carried out at room temperature and atmospheric pressure. Generally, it is preferred to carry out this reaction at a temperature of from 0° C. to 70° C.

The examples which follow further illustrate this invention. Unless otherwise stated, all examples were carried out under an atmosphere of argon. Unless otherwise stated, all temperature are in degrees Centigrade (°C.).

EXAMPLE 1

12.6 g of a 57% by weight sodium hydride/oil dispersion was washed three times with hexane under nitrogen and then heated at 70° C. with 70 ml. dimethylsulfoxide until all hydrogen evolution stopped. Obtained was a 4.2 molar solution of the sodium salt of dimethylsulfoxide in dimethyl sulfoxide.

EXAMPLE 2

61.2 g. trimethylsulfonium iodide was stirred with 130 ml. dry dimethylsulfoxide for about 30 min. and then treated with 100 ml. tetrahydrofuran to yield a fine suspension of the salt.

The suspension was cooled to 0° C., using an ice-ethanol bath, and treated over a period of 2 to 3 minutes with the sodium salt of dimethylsulfoxide in dimethyl sulfoxide prepared in Example 1.

The resulting grey colored suspension was then stirred for a further 4 min. at 0° C. and then treated with 38.4 g $\beta$-ionone [4-(2,6,6-trimethyl-1-cyclohexen-1-yl)-3-buten-2-one] dissolved in 50 ml. of tetrahydrofuran over a period of about 3 minutes. A dry ice-isopropanol bath was utilized to maintain the temperature of the reaction mixture at about 0°-5° C.

After complete addition of the $\beta$-ionone solution the mixture was stirred for 1 hour and, then, left to warm to room temperature (about 22° C.).

The mixture was then poured into 400 g. ice and extracted with one 300 ml. portion and two 200 ml. portions of hexane. The hexane extracts were then washed with water and dried over anhydrous sodium sulfate. Removal of the solvents "in vacuo" yielded 39.8 g. crude epoxide as a pale yellow colored liquid.

Distillation (4 inch vacuum jacketed Vigreaux column) gave 37.4 g. pure 1-(2,6,6-trimethyl-1-cyclohexenyl)-3SR-methyl-3,4-epoxy-but-1-ene; b.p. 75°-78° C./0.2 mmHg.

EXAMPLE 3

To a slurry, formed as in Example 2, from 91.2 g. trimethylsulfonium iodide in 450 ml. of a dimethylsulfoxide-tetrahydrofuran mixture (1:1 parts by volume), was added at 0° C. over about 3 minutes the sodium salt of dimethylsulfoxide, formed as in Example 1 from 18.9 g. of a 57% by weight sodium hydride/oil dispersion and 120 ml. of dry dimethylsulfoxide.

The mixture was stirred for 3 minutes at 0° C. and then treated with 38.4 g. 2,6,6-trimethylcyclohex-2-en-1-one, the temperature being held between $-5°$ C. and $+5°$ C. with a dry ice-isopropanol bath.

The resulting, light grey colored suspension was stirred for 1 hour and allowed to warm to room temperature. The suspension was then quenched with water and extracted into hexane. The hexane extracts were washed with water, dried over anhydrous sodium sulfate, and then concentrated at atmospheric pressure and a pot temperature of about 130° C.

Distillation of the reside (6 inch vacuum jacketed Vigreaux column) gave 37 g. pure (±)-4,8,8-trimethyl-1-oxaspiro[2,5]-oct-4-ene as a colorless liquid; b.p. 67°-68° C./8 mmHg.

EXAMPLE 4

150 mg. magnesium were treated with 0.54 ml. of dibromoethane in 10 ml. of diethyl ether. The resulting two phase system containing magnesium bromide was cooled to −10° C. and treated with 5 g. 1-(2,6,6-trimethyl-1-cyclohexenyl)-3SR-methyl-3,4-epoxy-but-1-ene, dissolved in 10 ml. diethyl ether. After 5 minutes at −10° C, the mixture was washed with water and dried over anhydrous sodium sulfate. Removal of the solvents "in vacuo" and distillation of the residue gave 3.9 g. (±) 1-(2,6,6-trimethyl-1-cyclohexenyl)-3-methyl-1-buten-4-al; b.p. 77°-80° C./0.2 mmHg.

EXAMPLE 5

6.18 g. (±) 1-(2,6,6-trimethyl-1-cyclohexenyl)-3-methyl-1-buten-4-al was dissolved in 15 ml. methanol and treated with 250 mg. KOH, dissolved in 0.3 ml. water and 5 ml. mathanol, and left at room temperature for 35 minutes. Extraction with hexane and water, followed by distillation, gave 4.75 g. 1-(2,6,6-trimethyl-1-cyclohexenyl)-3-methyl-2-buten-4-al; b.p. 85°-88° C/0.5 mmHg.

EXAMPLE 6

250 mg. magnesium was treated with 1.3 ml. dibromoethane in 25 ml. of diethyl ether. To the resulting two phase system containing magnesium bromide was added, at room temperature, 5 g. (±) 4,8,8-trimethyl-1-oxaspiro-[2,5]-oct-4-ene, dissolved in 20 ml. diethyl ether, and the resulting mixture was stirred for 45 minutes. The mixture was then washed with brine, dried over anhydrous sodium sulfate and finally distilled to give 4 g. of 2,6,6-trimethyl-2-cyclohexane-1-carboxaldehyde; b.p. 70°-72° C./8 mmHg.

EXAMPLE 7

Utilizing the procedure of Example 5, 4 g. 2,6,6-trimethyl-2-cyclohexene-1-carboxaldehyde was isomerized to form 4 g. of 2,6,6-trimethyl-1-cyclohexene-1-carboxaldehyde; b.p. 81°-88° C./8 mmHg.

EXAMPLE 8

By the procedure of Example 2; 6,10-dimethyl-3,5,9-undecatrien-2-one is converted to the epoxide, 2,6,10-trimethyl-1,2-epoxy-undeca-3 trans, 5 cis-trans, 9-triene (40.7 g.). Distillation gave the pure (cis,trans mixture about the $C_{5,6}$ double bond) epoxide (32.9 g.); b.p. 80°-85° C. at 0.1-0.2 mmHg.

EXAMPLE 9

By the procedure of Example 2; 6R, 10-dimetyl-2-oxo-undeca-3,9-diene (19.4 g.) was converted to 2SR, 6R, 10-trimethyl-1,2-epoxy-undeca-3,9-diene (20.3 g.).

EXAMPLE 10

By the procedure of Example 2; 6-methyl-hepta-3,5-trans-trans-dien-2-one was converted to 2SR, 6-dimethyl-1,2-epoxy-hepta-3,5-diene (2.6g.) as a mobile yellow-green colored liquid when subjected to the above reaction conditions. distillation yielded colorless material (85% yield) b.p. 33°-35° C. at 0.3 mmHg.

EXAMPLE 11

By the procedure of Example 2; 8(2,6,6-trimethyl-1-cyclohexen-1-yl)-6-methyl-3,5,7-octatrien-2-one (2.5 g.) was converted to (±) 1-)2,6,6-trimethyl-1-cyclohexen-1-yl)-3,7-dimethyl-7,8-epoxy-trans-cis/trans-trans-octa-1,3,5-triene (2.9 g.).

EXAMPLE 12

By the procedure of Example 2; citral (34.4 g.) was converted to (±) 4.8-dimethyl-1,2-epoxy-nona-3,7-diene (35.8 g.). Distillation of a portion (34.7 g.) of this material afforded pure material (28.9 g.) b.p. 60°-65° C. at 0.5 mmHg.

EXAMPLE 13

Magnesium (60 mg.) was converted to the bromide in diethyl ether (4 ml.) with dibromoethane (0.22 ml.), cooled to −10° C. and treated with 2,6,10-trimethyl-1,2-epoxy-undeca-3 trans,5 cis-trans, 9-trien (2 g.) dissolved in diethyl ether (4 ml.). After stirring for 10 minutes at −5° C. the reaction mixture was quenched with water and extracted with diethyl ether. Removal of the solvents "in vacuo" (about 35° C.) gave (±) 2,6,10-trimethyl-undeca-3,5,9-trien-1-al (2 g.).

EXAMPLE 14

The epoxide, 2SR,6-dimethyl-1,2-epoxy-hepta-3,5-diene (1.38 g.) in diethyl ehter (4 ml.) was added at 20° C. to magnesium bromide in diethyl ether (4 ml.). The magnesium bromide in diethyl ether was prepared from Mg (60 mg.) and $BrCH_2$—$CH_2$—Br (0.22 ml.). The temperature rose to −6° C. and the mixture was washed with water and extracted with more diethyl ether and distilled to yield the aldehyde, (±) 2,6-dimethyl-hepta-3,5-dien-1-al (1.27 g.) as a colorless liquid.

EXAMPLE 15

By the procedure of Example 4; the epoxide, (±) 1-(2,6,6-trimethyl-1-cyclohexen-1-yl)-3,7-dimethyl-7,8-epoxy-trans-cis/trans-trans-octa-1,3,5-triene (2.6 g.) was exposed to magnesium bromide in diethyl ether at −20° C. for 10 minutes. The reaction product was then worked up with water and diethyl ether and distilled in the manner of Example 13 to yield (±) 1-(2,6,6-trimethyl-1-cyclohexen-1-yl)-3,7-dimethyl-trans-cis/trans-trans-octa-1,3,5-trien-8-al (2.7 g.) as a pale yellow colored oil.

EXAMPLE 16

The epoxide, (±) 4,8-dimethyl-1,2-epoxy-nona-3,7-diene was converted by treatment with magnesium bromide by the procedure of Example 4, to 4,8-dimethyl-nona-3,7-dien-1-al. This conversion was carried out utilizing temperatures of −70° C. for a period of 5 minutes.

EXAMPLE 17

By the procedure of Example 5; 4,8-dimethyl-nona-3,7-dien-1-al is converted to 4,8-dimethyl-nona-2,7-dien-1-al.

EXAMPLE 18

A solution of the epoxide, 2SR,6R,10-trimethyl-1,2-epoxy-undeca-3,9-diene (13.7 g.) in diethyl ether (60 ml.) was added to magnesium bromide in diethyl ether.

The magnesium bromide was prepared from 500 mg. of magnesium, 2 ml. of dibromoethane in 60 ml. of diethyl ether. After the magnesium bromide had been added to the epoxide, the mixture was stirred for 5 minutes at −20° C. and then washed with water and extracted with diethyl ether. The ether extract was dried to yield 2,6R,10-trimethyl-3,9-undecadien-1-al.

EXAMPLE 19

The compound 2,6R,10-trimethyl-3,9-undecadien-1-al was dissolved in diethyl ether. To this ether extract, then was added 1.4 g. of potassium hydroxide dissolved in 50 ml. of aqueous methanol (1:1 parts by volume). The resulting mixture was stirred for 1 ½ hours at room temperature. After this period, the mixture was extracted with water and the aqueous extract was distilled to give 9.9 g. of 2,6R,10-trimethyl-2,9-undecadien-1-al b.p. 84°–86° C. at 0.5 mmHg.

EXAMPLE 20

By the procedure of Example 5; (±) 2,6,10-trimethyl-undeca-3,5,9-trien-1-al was converted to (±) 2,6,10-trimethyl-undeca-2,5,9-trien-1-al.

EXAMPLE 21

By the procedure of Example 5; (±) 2,6-dimethyl-hepta-3,5-dien-1-al is converted to (±) 2,6-dimethyl-hepta-2,5-dien-1-al.

EXAMPLE 22

By the procedure of Example 5; (±) 1-(2,6,6-trimethyl-1-cyclohexen-1-yl)-3,7-dimethyl-trans-cis/trans-trans-octa-1,3,5-trien-8-al is converted to (±) 1-(2,6,6-trimethyl-1-cyclohexen-1-yl)-3,7-dimethyl-trans-cis/-trans-trans-octa-1,3,6-trien-8-al.

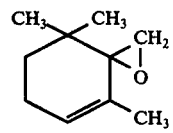

We claim:

1. A compound of the formula: